US00PP09399P

United States Patent [19]

Berry

[11] Patent Number: Plant 9,399

[45] Date of Patent: Dec. 12, 1995

[54] RAPHIOLEPIS INDICA VARIETY NAMED 'CONIA'

[75] Inventor: James B. Berry, Road-Daphne, Ala.

[73] Assignee: Flowerwood Nursery, Inc., Loxley, Ala.

[21] Appl. No.: 389,576

[22] Filed: Feb. 14, 1995

[51] Int. Cl.[6] ..... A01H 5/00

[52] U.S. Cl. ..... Plt./67.5

[58] Field of Search ..... Plt./67.5

*Primary Examiner*—James R. Feyrer

[57] ABSTRACT

A new and distinct variety of *Raphiolepis indica* found as an openly pollinated seedling of *Raphiolepis indica* 'Jack Evans'. The new variety is distinct with its large, thick, coriaceous leaves, rust colored tomentose new growth, stout stems, single, white flowers, improved cold hardiness, and increased resistance to leaf spot and fireblight.

2 Drawing Sheets

BACKGROUND OF THE INVENTION

This new variety of *Raphiolepis indica* was found as an openly pollinated seedling of *Raphiolepis indica* 'Jack Evans', an unpatented variety, maintained in the Flowerwood Nursery at Kelly Road, Loxley, Ala. The seedling was found in May 1987. The new and distinct *Raphiolepis indica* plant of this invention comprises a novel and valuable plant of loose, broad-mounding form, an abundance of white flower clusters, attractive rust colored new growth maturing to large glossy bright green leaves, stout stems, improved winter hardiness, and improved resistance to fireblight and leaf spot. The new variety has retained many of the outstanding attributes of its parent, in particular its tolerance of heat, drought, salt, insect, and diseases which makes it adaptable to culture in most of the Sunbelt States. As with the parent plant, the plant of this invention, which has been named 'Conia', may be advantageously employed as a specimen appointment, a ground cover, in either formal or informal groupings, and is quite attractive in mass plantings. The plant serves well in foundation plantings and is adapted for culture as a potted plant. This plant is responsive to pruning and training and may be employed in forming attractive hedges.

While evaluating the *Raphiolepis indica* 'Jack Evans' seedlings, attention was directed toward leaf spot and fireblight resistance. Any of the seedlings showing susceptibility to either disease were discarded. Cold hardiness was also a very important criterion. Plants of this seed group, as well as the parent, were evaluated in Alabama, Georgia, Florida, and Washington D. C. during the winters of 1991 and 1992. The new variety, *Raphiolepis indica* 'Conia' attained high levels of cold hardiness and maintained this level through the winter and into the early spring. This new variety showed the least amount of tip dieback of the selections tested.

Asexual propagation of the new plant by cuttings has been under Mr. Berry's direction at Flowerwood Nursery in Loxley, Ala. The increased number of plants were evaluated and demonstrated stability of the new characteristics from generation to generation. The plant cannot be reproduced true from seed.

SUMMARY OF THE INVENTION

The following are the most outstanding and distinguishing characteristics of this new cultivar when grown under normal horticultural practices in Loxley, Ala.

1. Loose and mounding in nature. Plant is wider than tall.
2. Moderate to slow growth rate.

3. New growth terminals are pronounced with a light rust coloration which offers a novel and strikingly appealing contrast of new foliage to old foliage in plants of this market class.
4. Hardy to Zone 7.
5. Heat and drought tolerant.
6. Good plant for coastal areas because of wind and salt tolerance.
7. Has shown good resistance to leaf spot and fireblight.
8. Relatively pest resistant.
9. Very desirable in planters.
10. Produces an abundance of large fruit in the summer which persist into the winter.
11. Large thick coriaceous leaves.
12. Flowers are single pure white, fragrant, and profuse.
13. The stem's caliper increases quickly.

DESCRIPTION OF THE DRAWING

The new variety of *Raphiolepis indica* is illustrated by the accompanying photographic prints in which.

1.

Figure 1:
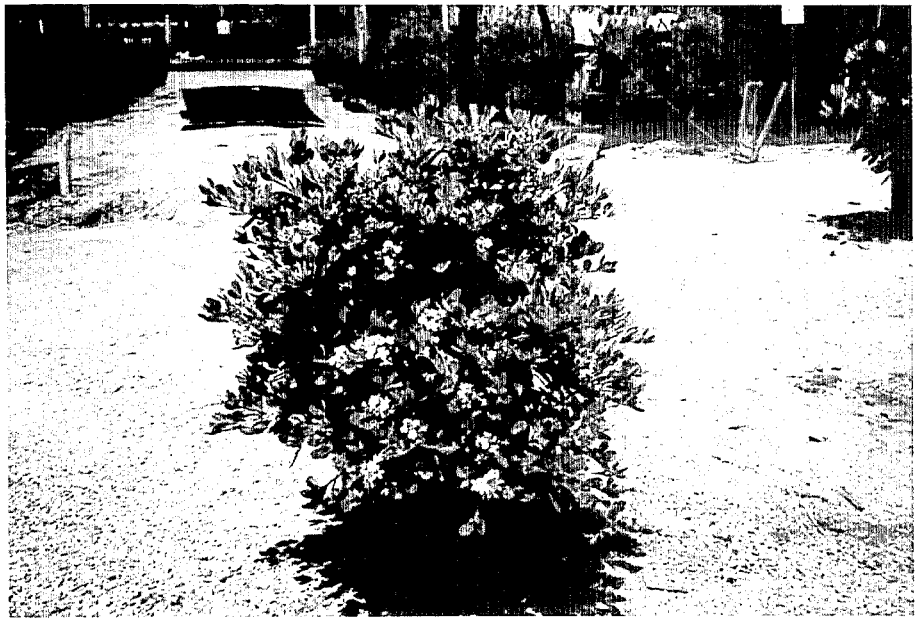
FIG. 1 discloses the loose, broad-mounding form.
2.
Figure 2:
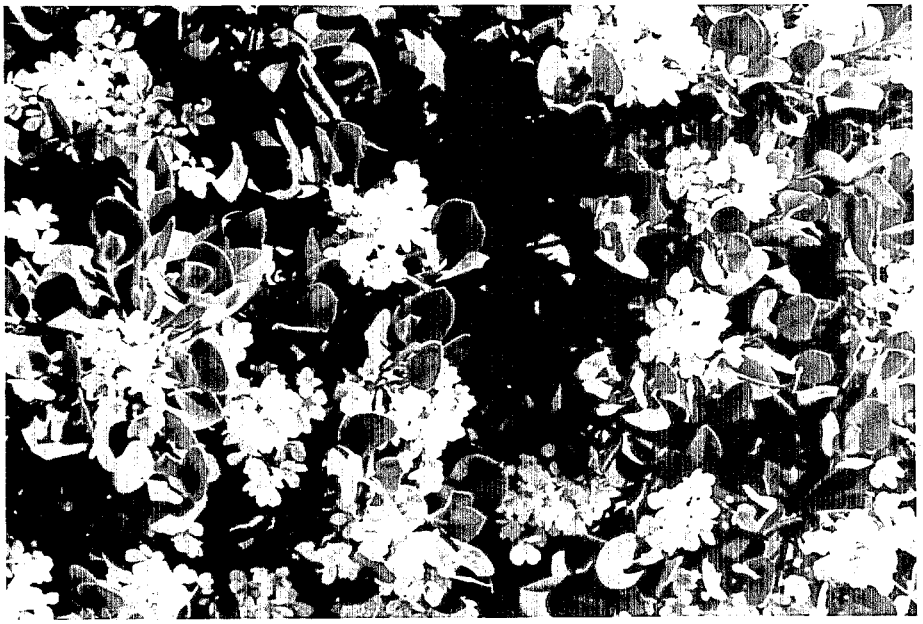
FIG. 2 is a close-up of the single white flowers and the rust colored new growth.
3.
Figure 3:
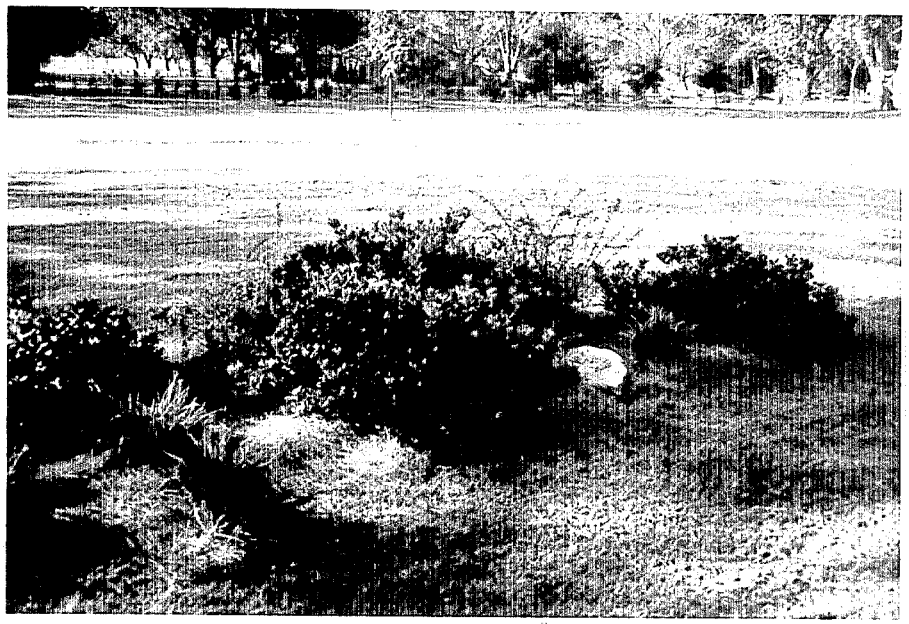
FIG. 3 shows the effective use and nature of use of the new variety in an established landscape planting.
4.
Figure 4:
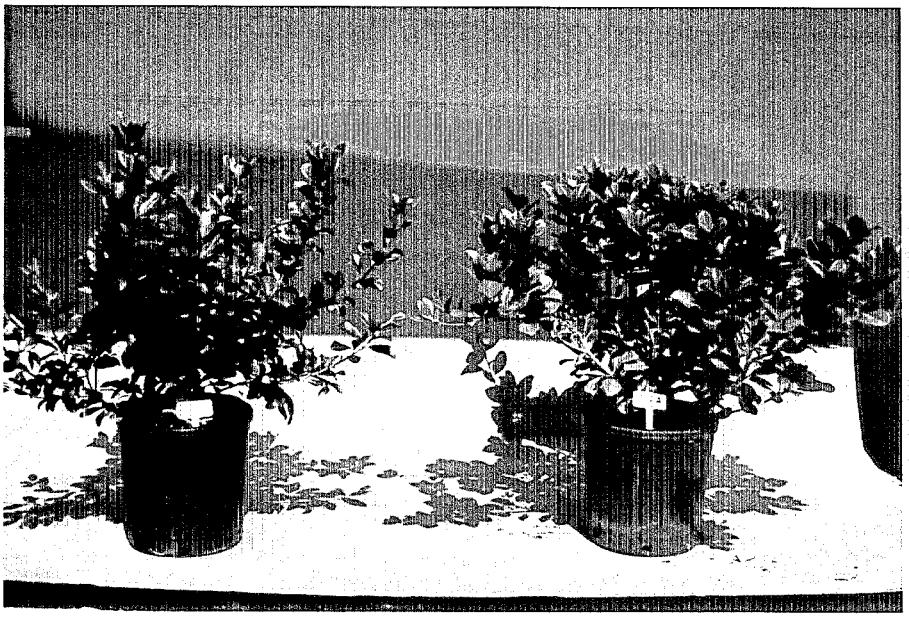
FIG. 4 is a side-by-side photograph of the parent variety *Raphiolepis indica* 'Jack Evans' (on the left) and the new variety (on the right). This photograph, which was taken in the late summer, shows the loose, broad-mounding form, the stout stems, and the large glossy bright green leaves of the new variety.

The colors shown are as true as is reasonably possible to obtain by conventional photographic procedures. The colors of the various plant parts are defined with reference to The Royal Horticultural Society Color Chart. Description of colors in ordinary terms are presented where appropriate for clarity in meaning.

BOTANICAL DESCRIPTION OF THE PLANT

The following is a detailed description of the new variety of *Raphiolepis indica* based on my observations made of plants grown in wholesale commercial production practices, in greenhouses, and established landscape plantings in Loxley, Ala.

| | Distinctive Characteristics: | | |
|---|---|---|---|
| Characteristic | 'Conia' | 'Jack Evans' | 'Snow White' |
| Height (Mature) | 3–4' | 4–5' | 2–3' |
| Width (Mature) | 4–5' | 4' | 3–4' |
| Leaf Length | 2¼–3½" | 2–3" | 2–3" |
| Leaf Width | 1¼–1¾" | 1–1½" | 1–1½" |
| Leaf Color (Immature) | Yellow-Green Group 152A | Greyed-Orange Group 177B | Yellow-Green Group 144A |
| Leaf Margin | Entire | Entire | Serrate to crenate |
| Leaf Curviture | Almost flat | Tip reflexed | Slightly undulate |
| Flower | Single | Single | Single |
| Flower Color | White Group 155D | Red-Purple Group 62B | White Group 155D |
| Petal Number | 5 | 5 | 5 |
| Petal Shape | Obovate | Elliptical | Obovate |

The plant from which all above varieties originated has the botonical name Rosaceae *Raphiolepis indica.* The author of the genus name Raphiolepis is John Lindley (1799–1865). The original author of the species name Indica is Carlolus Linnaeus (1707–1778) and the name was transferred to the plant *Raphiolepis indica* by John Lindley.

It is from the seedlings of the *Raphiolepis indica* 'Jack Evans' plant that I found the new plant. This new variety will be sold under the trademark name Olivia. It will be listed *Raphiolepis indica* Olivia TM 'Conia'.

*Raphiolepis indica* 'Snow White' is an unpatented variety which is very popular in the industry. It is comparable to the new plant in that both are low growing and have white blooms. However, there are many differences. The growth habit of 'Snow White' is more dense than the new variety. The mature leaf of the new variety is larger, darker, thicker, and flatter than 'Snow White' and the leaf margin is entire rather than serrate to crenate. The immature foliage of the new variety is tan and tomentose, whereas, 'Snow White' is light green and tomentulose.

Classification:

*Botanic.—Raphiolepis indica* 'Conia'.

Form: Loose and broad-mounding.

Texture: Coarse, rather stiff in appearance.

Size: In a period of six years from a rooted cutting the plant reaches a height of 3 feet and a spread of 4 feet. The plant normally grows at the rate of about 6 inches or more per year and reaches a height of 4 feet and spread of 5 feet at maturity.

Growth habit: Loose, mounding evergeeen shrub. Moderate to slow growth under normal fertilization and moisture conditions.

Foliage: Alternate, simple, evergreen, thick, elliptical to slightly obovate, and vary in size from 2¼–3½" long and 1¼–1¾" wide. The margins are entire, with a petiole ⅜–¾" long. The midrib is prominent on both sides of the leaf and the smaller veins are prominent on the underside. The base of the leaf is attenuates to cuneate and the apex is acute. The upper surface of the mature leaf is Yellow-Green Group 147A glossy and glabrous. The underside is Yellow–Green Group 146C and matte. The underside veins are Yellow-Green Group 146A. These mature leaf colors are persistant throughout the Winter. The immature leaves are tomentose, noticeably pigmented, and are Yellow-Green Group 152A. The paired foliaceous stipules are 3/16–⅜" long and 1/16–⅛" wide. The upper surface is Yellow-Green Group 145A and the underside is Yellow-Green Group 145B. The stipules are caducous.

In 1993, the date of initial Spring growth was March 4, in Loxley, Ala. After the initial Spring flush there was almost continuous slow growth until Fall ending, October 28, also in Loxley, Ala. This growth pattern was identical to the parent plant. When grown in full sun, the internode length of this plant and the parent plant is ½–¾". When grown in light shade the internode length is ⅝–1". As would be expected either plant grown in shade results in a taller less dense plant with larger leaves.

Stems: The young shoots have a reddish pigmentation, Greyed-Purple Group 183B and are tomentose. The base of the immature petioles are also Grey-Purple Group 183B. After one or more years the stems are generally grey, Greyed-Purple 197B, glabrous and rugose. The pith is solid and uniform. The stem's caliper increases quickly as the plant grows reaching a diameter of 3/16–¼" after one season's growth compared to the parent plant's stem caliper of ⅛–3/16".

Flowers: Perfect, single, White Group 155D ¾" diameter, fragrant, borns on dense, upright tomentose, 3½–4½" high and wide terminal panicles from March to April. Each panicle has from 3–9 racemes which have from 1–10 flowers each, resulting in 70 or more flowers per panicle. The flowers are attached to short pedicels which are 5/16–¾" in length. The peduncle of each The peduncle of each raceme is from ¼–½" long. Each flower has 5 petals that are ⅜" long and 5/16" wide, obovate, and have obtuse tips. The flower has from 15 to 20 stamen, ¼" long, with anthers Yellow-Group 9D. The pistil consists of 2 styles which are fused at the base or ovary. There are 5 sepals, Green Group 144B, which are united and have ciliate margins.

In 1993 the blooming period began March 14, in Loxley Ala. and ended May 2. Some blooms will appear in late May through October in southern Alabama.

Fruit: Drupelike pome, 7/16–⅝" diameter, 1 to 2 seeded berry. Summer fruit color Green Group 143B ripens to Greyed-Purple Group 187A in the Fall and persists as Black Group 202A attractively through the Winter.

Culture: Grows well in a wide range of conditions and tolerates sun to part shade. Grows in nearly any soil type, from moist to very dry and sand to clay. Responds well to mulching and medium applications of fertilizer; prefers ph 6 to 7. Very little pruning in needed. Adaptable to containers and above ground planters. Ideal for coastal regions and warmer parts of the Piedmont. Tolerates wind and salt spray. Propagated with semi-hardwood cuttings in late spring through the summer.

I claim:

1. A new and unique variety of *Raphiolepis indica* named *Raphiolepis indica* 'Conia' as herein shown and described, is characterized by its loose, broad-mounding form, large, thick coriaceous leaves, rust colored tomentose new-growth, abundance of single, fragrant white flowers and stout stems; the landscape value of this plant is increased by the improved cold hardiness and resistance to leaf spot and fireblight as well as its tolerance of heat, drought, wind, salt, insects, and soil type.

* * * * *